(12) United States Patent
Berner

(10) Patent No.: US 9,642,680 B2
(45) Date of Patent: May 9, 2017

(54) DENTAL IMPLANT

(71) Applicant: STRAUMANN HOLDING AG, Basel (CH)

(72) Inventor: Simon Berner, Suhr (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 14/896,586

(22) PCT Filed: Jun. 6, 2014

(86) PCT No.: PCT/EP2014/001547
§ 371 (c)(1),
(2) Date: Dec. 7, 2015

(87) PCT Pub. No.: WO2014/195025
PCT Pub. Date: Dec. 11, 2014

(65) Prior Publication Data
US 2016/0120626 A1 May 5, 2016

(30) Foreign Application Priority Data
Jun. 7, 2013 (EP) ..................................... 13002954

(51) Int. Cl.
*A61C 8/00* (2006.01)
*C22C 14/00* (2006.01)
(Continued)

(52) U.S. Cl.
CPC .......... *A61C 8/0015* (2013.01); *A61C 8/0075* (2013.01); *C22C 14/00* (2013.01);
(Continued)

(58) Field of Classification Search
CPC ... A61C 8/0015; A61C 8/0075; A61C 8/0006; A61C 2008/0046; A61C 2400/12;
(Continued)

(56) References Cited

U.S. PATENT DOCUMENTS

| 2002/0182567 A1 | 12/2002 | Hurson et al. |
| 2008/0220394 A1 | 9/2008 | Berckmans et al. |
| 2008/0261178 A1* | 10/2008 | Homann ............ A61C 8/0012 433/201.1 |

FOREIGN PATENT DOCUMENTS

| EP | 1 825 830 A1 | 8/2007 |
| FR | 2 931 056 A1 | 11/2009 |

(Continued)

OTHER PUBLICATIONS

Furuhashi, A. et al., "Influence of titanium surface topography on peri-implant soft tissue integration," Key Engineering Materials, 2013, pp. 559-564, vols. 529-530.

(Continued)

*Primary Examiner* — Pedro Philogene
*Assistant Examiner* — David C Comstock
(74) *Attorney, Agent, or Firm* — Oliff PLC

(57) ABSTRACT

A dental implant including a dental implant basic body extending along a longitudinal axis from an apical end to an opposite coronal end, which includes an anchoring part facing the apical end and intended to be anchored in bone of a patient, and a head part facing the coronal end and intended to form the basis on which a suprastructure is mounted. The anchoring part includes a shaft that is substantially cylindrical or that tapers toward the apical end in a cone-like manner. At least a portion of the shaft forms a bone tissue contact region, the outer surface forming a bone tissue contact surface. Coronally to the contact region a soft tissue contact region is arranged, the outer surface forming a soft tissue contact surface. The implant further includes nanostructures formed on the soft tissue contact surface which extend in at least two dimensions to 200 nm at most.

23 Claims, 2 Drawing Sheets

Figure 1:
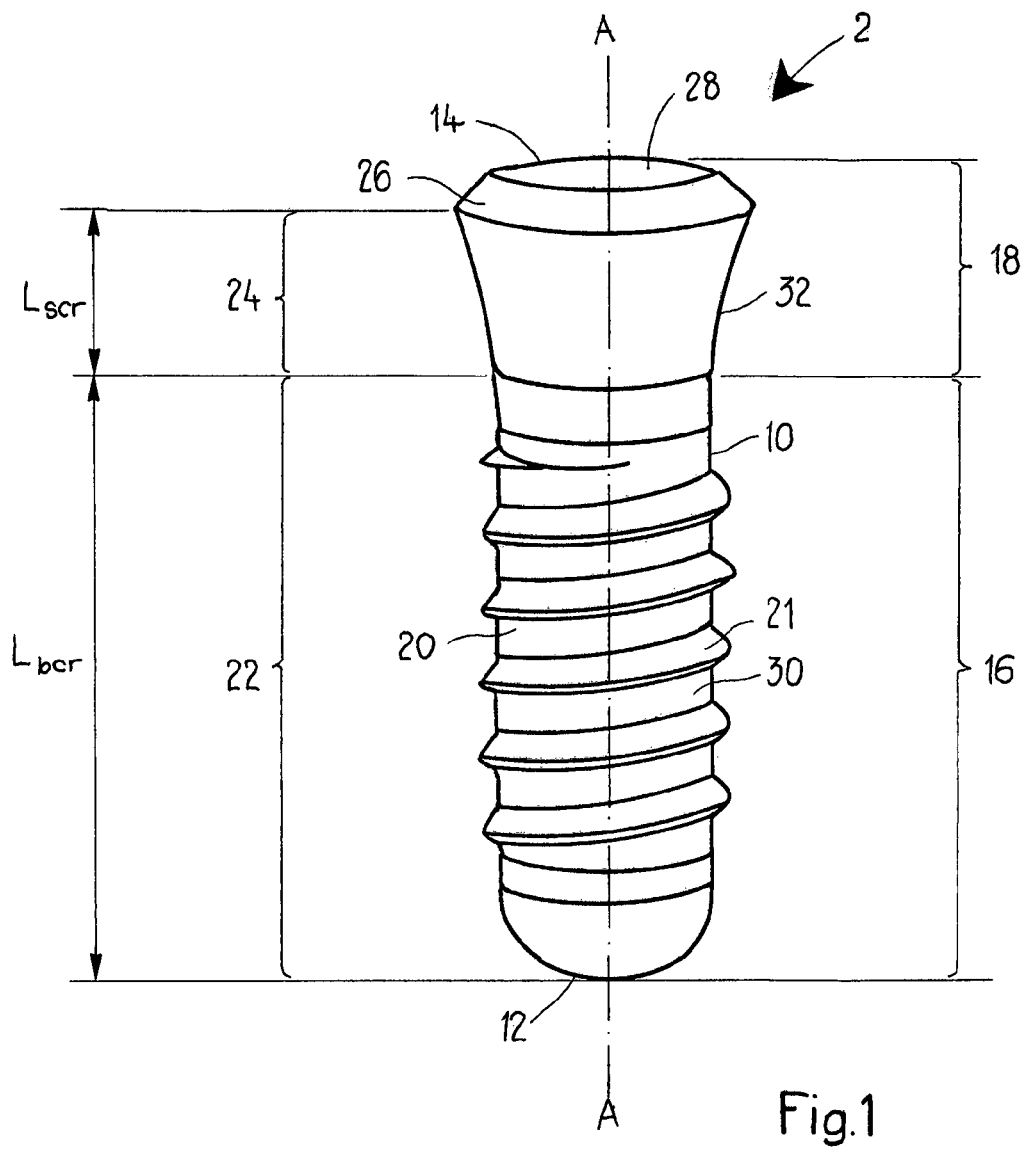

(51) Int. Cl.
    *C25D 5/00*     (2006.01)
    *C25D 5/38*     (2006.01)
    *C25D 7/00*     (2006.01)
    *A61C 8/02*     (2006.01)

(52) U.S. Cl.
    CPC ............... *C25D 5/00* (2013.01); *C25D 5/38* (2013.01); *C25D 7/00* (2013.01); *A61C 8/0006* (2013.01); *A61C 2008/0046* (2013.01); *A61L 2400/12* (2013.01); *A61L 2400/18* (2013.01); *A61L 2430/12* (2013.01)

(58) Field of Classification Search
    CPC . A61C 2400/18; A61C 2430/12; C22C 14/00; C25D 5/00; C25D 5/38; C25D 7/00
    USPC ...................................................... 433/201.1
    See application file for complete search history.

(56) References Cited

FOREIGN PATENT DOCUMENTS

| | | |
|---|---|---|
| WO | 2006/138352 A2 | 12/2006 |
| WO | 2013/056844 A1 | 4/2013 |

OTHER PUBLICATIONS

Dec. 9, 2014 International Search Report issued in International Patent Application No. PCT/EP2014/001547.

Dec. 8, 2015 International Preliminary Report on Patentability issued in International Patent Application No. PCT/EP2014/001547.

\* cited by examiner

DENTAL IMPLANT

The present invention relates to a dental implant comprising a dental implant basic body as well as to a process for providing sites of improved protein adherence on a dental implant basic body.

Dental implants are well known in the art. Generally, they comprise an anchoring part intended to be anchored in a patient's jaw bone and a head part intended to form the basis on which a suprastructure, such as a bridge or crown, is mounted. The mounting of the suprastructure is thereby often performed by using an intermediate, i.e. a so-called "secondary part" (also referred to as "abutment").

Apart from being biocompatible and having sufficient mechanical strength, it is required that the implant provides good osteointegration.

The term "osteointegration" designates the direct structural and functional connection between living bone and the surface of the implant. A good osteointegration means that the implant, after reaching a primary stability by screwing it into the bone, safely ossifies within a short healing time so that a permanent bond between implant and bone is obtained.

In the past, much effort has been made in order to improve the osteointegrative properties of implants.

Besides the importance of the implant's osteointegrative properties, there is on-growing evidence that also a good interaction between the implant and the surrounding supracrestal connective tissue (in the following referred to as the "soft tissue") is crucial for a successful implantation. This is supported by the view that the soft tissue plays a fundamental role in establishing an effective seal between the oral environment and the endosseous part of a dental implant and, thus, also a barrier for bacteria to adhere on the soft tissue contact surface and the bone tissue contact surface of the implant.

Indeed, the presence of bacteria on the implant surface may lead to an inflammation of the peri-implant mucosa, and, if left untreated, the inflammation spreads apically and results in bone resorption.

As a consequence of the theory that rough surfaces accumulate and retain more plaque than smooth surfaces (see Oral Implantology, Thieme Verlag, 1996, page 438), nowadays, the soft tissue contact surface of implants is typically machined.

As mentioned above, the soft tissue contact surface would ideally not only provide a surface showing a low tendency for bacteria to adhere, but also allow a relatively strong and fast interaction between the soft tissue and the implant to be established (also referred to as "soft tissue integration"), in order to quickly provide an effective seal between the oral environment and the endosseous part.

Aiming at an improved soft tissue integration of the implant, EP-A-1825830 suggests a soft tissue contact surface that is at least partially hydroxylated or silanated. In this context, improved soft tissue integration is explained by the loose connective tissue to become organized and replaced be newly formed collagen fibers.

Irrespective of the beneficial effects achieved by the technology described in EP-A-1825830, there is an on-going need for further, simple solutions for improving soft tissue integration of the dental implant.

The object of the present invention is thus to provide a dental implant having a soft tissue contact surface which establishes a good soft tissue integration, i.e. a relatively strong interaction between implant and soft tissue in a relatively timely manner, and which at the same time shows a low tendency for bacteria to adhere.

This problem is solved by the subject matter of claim 1. Preferred embodiments of the invention are subject of the dependent claims.

According to claim 1, the present invention relates to a dental implant comprising a dental implant basic body extending along a longitudinal axis A from an apical end to a coronal end arranged opposite to the apical end.

The dental implant basic body comprises an anchoring part facing the apical end and intended to be anchored in bone of a patient, and a head part facing the coronal end and intended to form the basis on which a suprastructure is mounted. The head part can thereby be designed such to allow the suprastructure to be mounted directly or indirectly, i.e. using at least one intermediate, as it is the case in multi-part dental implant systems.

The anchoring part comprises a shaft having a basic form that is substantially cylindrical or that tapers in the direction toward the apical end in a cone-like manner. At least a portion of the shaft forms a bone tissue contact region, the outer surface of which forming a bone tissue contact surface.

Coronally to said bone tissue contact region a soft tissue contact region is arranged, the outer surface of which forming a soft tissue contact surface. The soft tissue contact region can be arranged coronally adjacent to the bone tissue contact region. Alternatively, a transition region can be arranged between these regions.

According to the invention, the dental implant comprises nanostructures formed on the soft tissue contact surface, said nanostructures extending in at least two dimensions to 200 nm at most.

These nanostructures form retention sites, allowing for an improved initial adherence of proteins of the cells of the surrounding soft tissue. Without wanting to be bound by the theory, transmembrane proteins, specifically integrins, can directly or indirectly, i.e. by mediation of other proteins, adhere to the nanostructures and, thus, establish an anchorage of the cells to the implant's soft tissue contact surface. In this complex mechanism, laminins, which is linked with the extracellular domain of the integrins, can also play an important role, as well as plasma proteins, such as albumin, fibrinogen and fibronectin.

Ultimately, the nanostructures forming retention sites allow for an optimal soft tissue interaction of the implant and, consequently, an effective seal between its endosseous part and the oral environment to be achieved.

According to a particularly preferred embodiment, the soft tissue contact surface of the dental implant basic body on which the nanostructures are formed is smooth, e.g. machined or polished.

In other words, the surface topography is smooth when regarded in macroscopic and microscopic scale, but nevertheless provides a nanoscopic structure due to the presence of the nanostructures. These nanostructures are small enough not to interfere with the low plaque forming tendency of the soft tissue contact surface, but big enough to allow proteins of the surrounding soft tissue cells to adhere. As a result, the soft tissue contact surface's tendency for adherence of bacteria is low, while at the same time protein adherence of the surrounding soft tissue cells can take place.

Alternatively to the soft tissue contact surface of the dental implant basic body being smooth, it can also be minimally rough, i.e. having a roughness as e.g. obtainable by acid etching.

The term "dental implant" as used in the context of the present invention relates to the primary part of a dental implant system, i.e. the part that is actually implanted in the bone.

In that the soft tissue contact surface of the dental implant basic body is preferably smooth, it is in clear distinction from the bone tissue contact surface, which typically comprises a macroscopic topography, achieved e.g. by sandblasting and/or machining, as well as a microscopic topography, achieved e.g. by acid etching.

According to a further preferred embodiment, the soft tissue contact region widens in the direction towards the coronal end, and, more particularly, widens in a cup shape. In this embodiment, the transition from the bone tissue contact surface to the soft tissue contact surface is even more apparent.

It is further preferred that the bone tissue contact region extends from the apical end in the direction to the coronal end in a length $l_{bcr}$ ranging from 4 to 16 mm.

Given the typical ranges of the length of a dental implant, the soft tissue contact region, thus, preferably extends from the respective end of the bone tissue contact region in direction to the coronal end a length $l_{scr}$ ranging from 1 mm to 3 mm.

The ratio of $l_{bcr}$ to the total length $l_{tot}$ of the dental implant depends on the specific type of the dental implant used. Preferably, $l_{bcr}$ corresponds to about 55% to 95% of the total length $l_{tot}$ of the dental implant.

It is understood that the present invention encompasses dental implants in which nanostructures are formed on the soft tissue contact surface only, as well as embodiments in which they are formed on the surface of additional regions than the soft tissue contact region, and embodiments in which they are formed on the whole surface of the dental implant basic body.

As mentioned above, the present invention encompasses both dental implants for a one-part dental implant system as well as dental implants for a multi-part dental implant system, specifically a two-part dental implant system. In particular in case of a two-part dental implant system, the head part of the dental implant basic body preferably comprises a shoulder functioning as a support for the abutment. It is particularly preferred that the outer surface of this shoulder is also smooth in order to prevent any "micro-gaps" between the dental implant and the abutment.

According to a further preferred embodiment, the nanostructures are at least predominantly in crystalline phase. More preferably, the nanostructures are in an at least approximately purely crystalline phase.

The nanostructures can have different shapes including a needle-like shape, a leaf-like shape, a flower-like shape, a sphere-like shape or a nodule-like shape.

In the context of the present invention, the term "needle-like shape" encompasses any shape having a length to diameter ratio of more than 1:1. Thereby, the diameter is to be understood as the expansion of the nanostructure in a direction perpendicular to the longitudinal direction.

Preferably, the nanostructures have an average length-to-diameter ratio of more than 1 to 1, more preferably of at least 1.5 to 1, most particularly ranging from 1.5 to 1 to 4 to 1.

As mentioned, the nanostructures according to the present invention preferably extend in at least two dimensions to 200 nm at most. More specifically, the nanostructures preferably have an average diameter of about 10 nm to 150 nm and an average length of about 5 nm to 500 nm.

It has further been found that by the presence of nanostructures, a relatively high hydrophilicity can be achieved, which can further contribute to a good soft tissue interaction. According to a preferred embodiment, the soft tissue contact surface, thus, has a hydrophilicity defined by a contact angle of less than 90°, more preferably less than 30°, most preferably less than 10°, when contacted with water.

It is further preferred that the dental implant basic body is made of titanium or a titanium alloy. A respective basic body allows nanostructures to be formed on its surface in a relatively simple and reproducible manner, as will be shown below.

In view of its use in the field of implantology, and in particular oral implantology, any suitable grade of titanium or titanium alloy known to the skilled person can be used, including titanium of grade 2 to grade 4.

When using a titanium alloy, this is preferably a titanium zirconium (TiZr) alloy, typically comprising Zr in an amount of 13 to 17%. Alternatively, a titanium aluminium vanadium alloy, specifically Ti-6Al-4V (TAV), or a titanium aluminium niobium alloy, specifically Ti-6Al-7Nb (TAN), can be used as a titanium alloy suitable for the purpose of the present invention.

With regard to the use of titanium or a titanium alloy for the dental implant basic body, it is further preferred that the nanostructures comprise titanium hydride and/or titanium oxide.

In case the nanostructures comprise titanium hydride, they typically comprise $TiH_2$, whereas in case the nanostructures comprise titanium oxide, they typically comprise $TiO_2$.

According to a further aspect, the present invention also relates to a process for providing sites of improved protein adherence on a dental implant basic body, as described above.

According to this process, the nanostructures are grown on the soft tissue contact surface by treating the soft tissue contact surface with an aqueous solution.

The feature that the nanostructures are grown means that they are not formed by a mechanical removing process or by subjecting the surface of the body to other mechanical structuring processes. Rather, the formation of the nanostructures occurs gradually in that they "build up" over time by treating the soft tissue contact surface with the aqueous solution.

The term "aqueous solution" as used in the context of the present invention encompasses both pure water as well as a solution in which the solvent is water.

A particularly good formation/growing of nanostructures has been observed for embodiments in which the aqueous solution is an acidic solution comprising at least one component selected from the group consisting of hydrogen fluoride, nitric acid, hydrochloric acid, sulphuric acid, tartaric acid, oxalic acid, citric acid and acetic acid, and/or mixtures thereof.

As mentioned above, the dental implant basic body is typically made of titanium or a titanium alloy.

According to a well-controllable and thus preferred process, the growing of the nanostructures is performed by cathodic polarization (also referred to as "cathodic hydridation"), in which the dental implant basic body forms the cathode. A detailed description of this process will be given by way of the examples below.

In this regard, it is particularly preferred that before performing cathodic polarization, the soft tissue contact surface is pickled with a pickling solution in order to at least partially remove a titanium oxide layer present on the soft tissue contact surface. A pickling solution comprising at least one component selected from the group consisting of nitric acid, hydrofluoric acid, ammonium fluoride, hydrochloric acid and sulphuric acid, and/or mixtures thereof, particularly a mixture of nitric acid and hydrofluoric acid, is thereby preferably used.

With regard to the cathodic polarization, this is preferably performed in a buffer having a pH in the range from 0 to 6. The temperature is preferably set in a range from 5 to 95° C., preferably from 10 to 75° C., more preferably from 15 to 50° C., most preferably at about room temperature.

Additionally or alternatively to the above described process using cathodic polarization, the nanostructures can be grown by storing the soft tissue contact surface in the aqueous solution.

The storing is typically carried out by using a 0.9% NaCl solution, more specifically having a pH of 2 to 7, preferably 3 to 6. Likewise, any other suitable aqueous solution can be used including pure water.

According to a particularly preferred embodiment, the storing is carried out for at least one month, more preferably at least two months, most preferably at least four months. The storage time depends on the surface topography of the soft tissue contact surface of the dental implant basic body. For a machined surface, the storage times required for the growing of the nanostructures has been found to be longer than for a rough surface. However, also for a machined soft tissue contact surface nanostructures are detected after two months of storing.

With regard to the storing, it is further preferred that this is performed at an elevated temperature, i.e. a temperature above room temperature, since nanostructure formation has been shown to be particularly pronounced at these temperatures.

A temperature in a range of about 50° C. to 250° C., more particularly about 100° C. to 180° C., and most preferably about 120° C. to 150° C. has been shown to be particularly preferred, since the storing time required for the growing of nanostructures can be shortened substantially. A storing over months is, thus, not required when performing a (hydro-) thermal treatment at the temperatures specified above.

It is understood that the process of the present invention encompasses embodiments in which only the soft tissue contact region is subjected to the treatment with the aqueous solution, as well as embodiments in which additional regions and embodiments in which the whole surface are/is subjected to this treatment.

As also mentioned above, the bone tissue contact surface is preferably roughened and comprises a macroscopic topography, achieved e.g. by sand-blasting and/or machining, as well as a microscopic topography, achieved e.g. by acid etching.

The process of the present invention, thus, preferably comprises the further step of roughening the surface of at least a portion of the dental implant basic body, in particular by sand-blasting, machining and/or acid-etching, and more particularly by sand-blasting and/or machining followed by acid-etching. Instead of the sand-blasting or machining, injection moulding techniques are also thinkable to provide a macroscopic roughness. For the acid-etching step, a mixture of HCl and $H_2SO_4$ is preferably used.

According to one preferred embodiment, only the bone tissue contact surface is roughened. This way, a dental implant can be achieved which on the one hand has a highly osteointegrative bone tissue contact surface and on the other hand a soft tissue contact surface with low plaque adherence tendency in addition to an improved soft tissue interaction.

Irrespective of the above described embodiment, in which only the bone tissue contact surface is roughened, embodiments in which the soft tissue contact surface is roughened, e.g. by acid etching, are also encompassed by the present invention. Depending on the actual aim to be achieved, these embodiments can also be preferred, since nanostructure formation has been shown to be favoured on a roughened surface.

Figure 2:
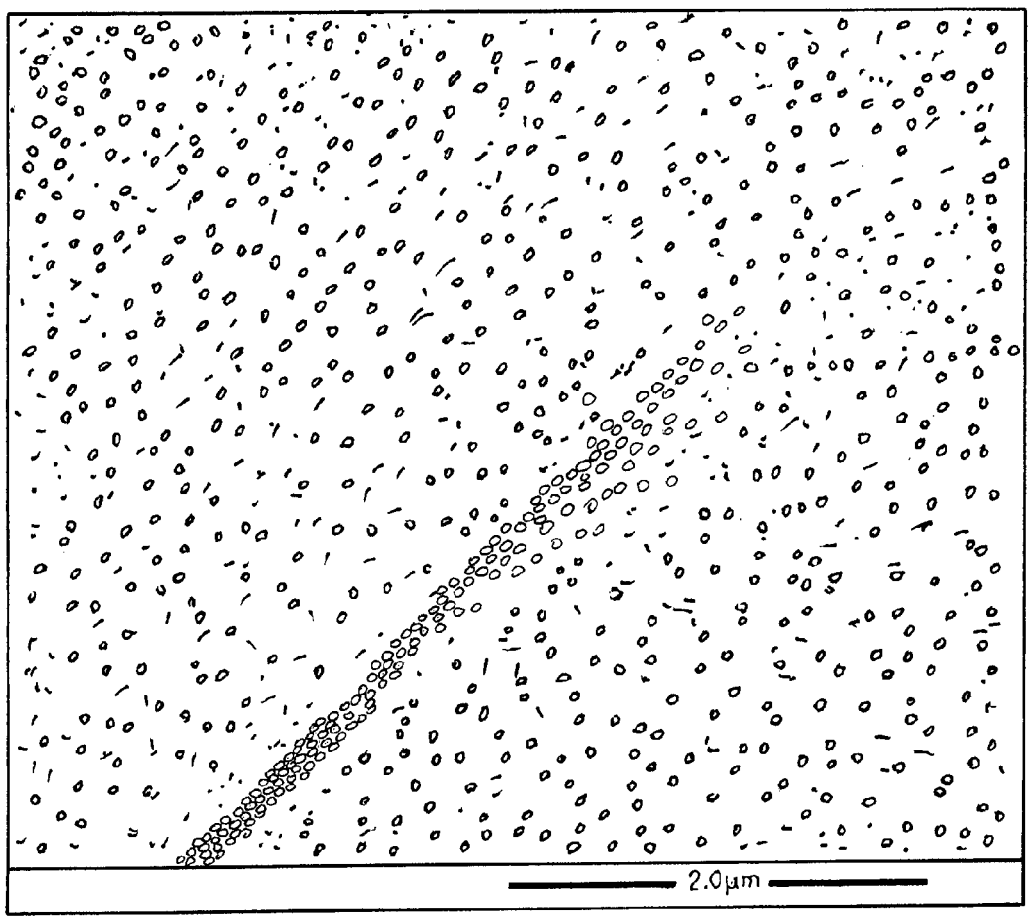

The present invention is further illustrated by way of the attached figures, of which FIG. 1 shows a dental implant according to the present invention, comprising a dental implant basic body with nanostructures formed on the soft tissue contact region; and FIG. 2 shows a picture of the soft tissue contact surface of a dental implant according to the present invention, said picture being obtained by Field Emission Scanning Electron Microscopy.

The dental implant 2 shown in FIG. 1 comprises a dental implant basic body 10, which extends along a longitudinal axis A from an apical end 12 to a coronal end 14 arranged opposite to said apical end.

In the apical end region, the dental implant basic body 10 comprises an anchoring part 16 which is intended to be anchored in bone of a patient.

In the coronal end region, the dental implant basic body 10 comprises a head part 18, which is intended to form the basis on which a suprastructure is mounted.

The anchoring part 16 comprises a shaft 20, which has a basic form that is substantially cylindrical tapering into a rounded tip towards the apical end 12 and on which an outer thread 21 is formed. The shaft 20 forms a bone tissue contact region 22 which extends from the apical end 12 in the direction to the coronal end 14, i.e. in longitudinal direction, in a length $l_{bcr}$ and which is destined to be in contact with bone when in the implanted state.

Coronally adjacent to the bone tissue contact region 22 a soft tissue contact region 24 is arranged, which from the respective end of the bone tissue contact region 22 extends in the direction to the coronal end 14, i.e. in longitudinal direction, in a length $l_{scr}$ and thereby widens in a cup shape.

At the outermost coronal end 14 of the dental implant basic body 10 and directly adjacent to the soft tissue contact surface, a shoulder 26 is formed, which frusto-conically tapers towards the coronal end 14. Further, the coronal end 14 is provided with a recess 28, into which a abutment (not shown) can be fitted.

The outer surface of the bone tissue contact region 22 forms a bone tissue contact surface 30, which typically has an osteointegrative surface topography, e.g. obtainable by sand-blasting and subsequent acid-etching.

The outer surface of the soft tissue contact region 24 forms a soft tissue contact surface 32. On the soft tissue contact surface 32, nanostructures are formed, which will be illustrated by way of FIG. 2.

In an alternative to the embodiment shown in FIG. 1, in which the soft tissue contact surface 24 widens in direction to the coronal end 14, it is also possible for the soft tissue contact region to be cylindrical and/or to be kept very short.

During implantation, the bone tissue contact region 22 is preferably embedded completely in the bone of the patient and—after implantation—is therefore surrounded by the bone. A rapid development of a primary stability is thereby achieved by the outer thread 21 engaging in the bone of the patient.

During the healing period, the bone tissue contact region 22 ossifies with the bone, while the soft tissue contact region 24 with the nanostructures formed thereon interacts with the soft tissue surrounding the dental implant 2. In this regard, the nanostructures function as sites of improved protein adherence, in particular for transmembrane proteins, more particularly integrins, of the surrounding soft tissue cells.

After the healing period, a suprastructure can be mounted on the head part 18 of the dental implant 2. This is typically done with the aid of an abutment, which is fixed in a manner known per se by retaining means, typically a screw, the outer thread of which cooperates with an inner thread (not shown) formed in the recess 28. In order not to allow any "microgaps" to be present between the shoulder 26 and the abutment, the outer surface of the shoulder 26 supporting the abutment is typically smooth.

Alternatively to these two-part dental implant systems, the dental implant system can also be a one-part dental implant system, in which no separate secondary part/abutment is used as mounting part but in which the mounting part is formed in one piece with the dental implant.

EXAMPLES

Treatment of the Samples

Titanium samples were grinded and polished and were then washed with NaOH at 40% (w/v) and $HNO_3$ at 40% (w/v) in an ultrasonic bath to remove contaminants, then washed with deionized water to reach a neutral pH and stored at room temperature in 70 vol.-% ethanol.

After the polishing and cleaning steps, some of the samples were treated ("pickled") for one minute in a solution containing 15 wt.-% $HNO_3$ and 5 wt.-% HF (solution C1) at room temperature (samples p1). Alternatively, samples were treated in a solution C1 diluted twice with deionized water (samples p2), diluted five times with deionized water (samples p5) and diluted ten times with deionized water (samples p10).

Immediately after the pickling treatment, the samples were washed by dipping in a beaker containing deionized water for 10 seconds, then mounted on a sample holder forming a cathode for cathodic polarization (or cathodic hydridation).

For the cathodic hydridation, current densities at 5, 10 and 15 $mA/cm^2$ were used. The hydration was performed at room temperature and the duration of the hydridation was set to 0.5, 2 and 5 hours. As electrolyte, tartaric acid at 1 M of concentration, pH 1.9, was used.

Nanoscale Analysis of the Samples

Following the hydridation step, a nanoscale analysis of each of the modified surfaces was performed using a Field Emission Scanning Electron Microscope (FE-SEM; Quanta 200F, FEI, The Netherlands).

As an example for the pictures obtained, FIG. 2 shows the surface of sample p1, with the cathodic polarization being performed at a current densities of 5 $mA/cm^2$ and with the duration of the hydridation being set to 0.5 hours.

As given in the picture, the ruler at the bottom of the picture corresponds to 2 μm. The white "spots" show the nanostructures, in the particular case nano-nodules, with a diameter well below 200 nm. These form retention sites for improved protein adherence of the surrounding soft tissue.

The invention claimed is:

1. A dental implant comprising a dental implant basic body extending along a longitudinal axis A from an apical end to a coronal end arranged opposite to the apical end, said dental implant basic body comprising
an anchoring part facing the apical end and intended to be anchored in bone of a patient, and
a head part facing the coronal end and intended to form the basis on which a suprastructure is mounted,
said anchoring part comprising a shaft having a basic form that is substantially cylindrical or that tapers in a direction toward the apical end,
at least a portion of the shaft forming a bone tissue contact region, the outer surface of which forms a bone tissue contact surface, and
a soft tissue contact region being arranged coronally to said bone tissue contact region, the outer surface of the soft tissue contact region forms a soft tissue contact surface,
wherein
the dental implant further comprises nanostructures formed on the soft tissue contact surface, said nanostructures extending in at least two dimensions to 200 nm at most; and
the soft tissue contact surface is macroscopically and microscopically smooth.

2. The dental implant according to claim 1, wherein the soft tissue contact surface of the dental implant basic body on which the nanostructures are formed is machined or polished.

3. The dental implant according to claim 1, wherein the dental implant basic body is made of titanium or a titanium alloy.

4. The dental implant according to claim 1, wherein said nanostructures comprise titanium hydride and/or titanium oxide.

5. The dental implant according to claim 1, wherein the nanostructures are at least predominantly in crystalline phase.

6. The dental implant according to claim 1, wherein the nanostructures have an average length-to-diameter ratio of more than 1 to 1.

7. The dental implant according to claim 1, wherein the nanostructures have an average diameter of about 10 nm to 150 nm and an average length of about 5 nm to 500 nm.

8. The dental implant according to claim 1, wherein the soft tissue contact surface has a hydrophilicity defined by a contact angle of less than 90° when contacted with water.

9. The dental implant according to claim 1, wherein the bone tissue contact region extends from the apical end in a direction to the coronal end in a length $l_{bcr}$ ranging from 4 to 16 mm.

10. The dental implant according to claim 1, wherein the soft tissue contact region extends from a respective end of the bone tissue contact region in a direction to the coronal end in a length $l_{scr}$ ranging from 1 mm to 3 mm.

11. A process for providing sites of improved protein adherence on a dental implant basic body extending along a longitudinal axis A from an apical end to a coronal end arranged opposite to the apical end, said process comprising
growing nanostructures on a soft tissue contact surface of the dental implant basic body by treating the soft tissue contact surface with an aqueous solution;
wherein
the dental implant basic body comprises:
an anchoring part facing the apical end and intended to be anchored in bone of a patient, and
a head part facing the coronal end and intended to form the basis on which a suprastructure is mounted,
said anchoring part comprises a shaft having a basic form that is substantially cylindrical or that tapers in a direction toward the apical end, at least a portion of the shaft forms a bone tissue contact region, the outer surface of which forms a bone tissue contact surface, a soft tissue contact region is arranged coronally to said bone tissue contact region, the outer surface of the soft tissue contact region forms the soft tissue contact surface on which the nanostructures are grown, and the soft tissue contact surface is macroscopically and microscopically smooth.

12. The process according to claim 11, wherein the dental implant basic body is made of titanium or a titanium alloy.

13. The process according to claim 11, wherein the aqueous solution is an acidic solution comprising at least one component selected from the group consisting of hydrogen fluoride, nitric acid, hydrochloric acid, sulphuric acid, tartaric acid, oxalic acid, citric acid, acetic acid, and mixtures thereof.

14. The process according to claim 11, wherein the growing of the nanostructures is performed by cathodic polarization, in which the dental implant basic body forms the cathode.

15. The process according to claim 14, wherein the soft tissue contact surface is pickled with a pickling solution in order to at least partially remove a titanium oxide layer present on the soft tissue contact surface before performing the cathodic polarization.

16. The process according to claim 15, wherein the pickling solution comprises at least one component selected from the group consisting of nitric acid, hydrofluoric acid, ammonium fluoride, hydrochloric acid, sulphuric acid, and mixtures thereof.

17. The process according to claim 14, wherein the cathodic polarization is performed in a buffer having a pH in a range of from 0 to 6.

18. The process according to claim 14, wherein the cathodic polarization is performed at a temperature in a range of from 5 to 95° C.

19. The process according to claim 11, wherein the nanostructures are grown on the soft tissue contact surface by storing the soft tissue contact surface in the aqueous solution.

20. The process according to claim 19, wherein the storing is performed for at least one month.

21. The process according to claim 19, wherein the storing is performed above room temperature.

22. The process according to claim 11, further comprising roughening the bone tissue contact surface of the dental implant basic body.

23. The process according to claim 22, wherein the bone tissue contact surface is roughened by sand-blasting, machining, acid-etching, or combinations thereof.

* * * * *